United States Patent [19]

Xu

[11] Patent Number: 5,616,484

[45] Date of Patent: Apr. 1, 1997

[54] CLONING AND EXPRESSION OF THE APALI RESTRICTION ENDONUCLEASE

[75] Inventor: Shuang-yong Xu, Lexington, Mass.

[73] Assignee: New England Biolabs, Inc., Beverly, Mass.

[21] Appl. No.: 448,744

[22] Filed: May 24, 1995

[51] Int. Cl.$^6$ .............................. C12N 9/22; C12N 15/55
[52] U.S. Cl. .................. 435/199; 435/320.1; 435/252.3; 435/193; 536/23.2
[58] Field of Search .................................... 435/199, 193, 435/320.1, 252.3, 252.33; 536/23.2

[56] References Cited

U.S. PATENT DOCUMENTS 4,833,082  5/1989  Yamada et al. ......................... 435/199

FOREIGN PATENT DOCUMENTS 193413  3/1986  European Pat. Off. .

OTHER PUBLICATIONS

Kosykh, et al., Molec. Gen. Genet. 178:717–718 (1980).
Mann, et al., Gene, 3:97–112 (1978).
Walder, et al., Proc. Natl. Acad. Sci. USA, 78:1503–1507 (1981).
Bougueleret, et al., Nucl. Acids Res. 12:3659–3676 (1984).
Gingeras and Brooks, Proc. Natl. Acad. Sci. USA, 80:402–406 (1983).
Theriault and Roy, Gene, 19:355–359 (1982).
Blumenthal, et al., J. Bacteriology, 164:501–509 (1985).
Kiss, et al., Nucl. Acids Res. 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Fomenkov, et al., Nucl. Acids Res., 22:2399–2403 (1994).
Raleigh and Wilson, Proc. Natl. Acad. Sci. USA 83:9070–9074 (1986).
Heitman and Model, J. Bact. 169:3243–3250 (1987).

Primary Examiner—Charles L. Patterson, Jr.
Attorney, Agent, or Firm—Gregory D. Williams

[57] ABSTRACT

The present invention relates to a method of cloning ApaLI methylase gene (apaLIM) and ApaLI endonuclease gene (apaLIR) from *Acetobacter pasteurianus* into *E. coli* by the methylase selection method and inverse PCR. The ApaLI methylase gene was cloned into pUC19 (3 ApaLI sites inserted) by the methylase selection method. Eight ApaLI-resistant clones were isolated and found to contain apaLIM gene. However, these clones are not stable such that sometimes overnight cultures were lysed or plasmid DNA was lost in the unlysed culture.

7 Claims, 3 Drawing Sheets

ApaLI methylase gene sequence

```
   1  ATGAATAAGG ACGAAGTTGT TGTATCTCTG TTTGCTGGGG CTGGGGGATT
  51  CTCCTCTGGC TTTAGTCAGG CTGGTCTGAA GCCTTTATTT GGTGCGGAAA
 101  TTAACGCTGA TGCCTGCCAG ACTTACCAAG AGAATGTCGG CAGCCCCTGC
 151  CACCAGCTTG ATCTGAGCAC GGTTGACCCA TCTCATATTG AAATGCTCAC
 201  GGGTGGCAAA AGGCCGTTCG TCGTTATTGG CGGGCCGCCG TGCCAAGGCT
 251  TTAGTACCGC TGGTCCGCGC AATTTTGCAG ATCCTCGCAA TCTGCTCATT
 301  TTTAACTACT TAAATATCGT TGAGCGGCTT TCGCCCCGTT GGCTCATTTT
 351  CGAAAATGTC GAAGGACTTT TGACGTCTGG TGGGGGGCGG GACCTTGCGC
 401  GTCTGGTACG AGAGTTTGTC GACATGGGAT ATTCGGTACG GCTCCAAAAG
 451  GTAAACCTAG CCGCATATGG CGTGCCACAA ACGCGTAAGC GGGTGCTAAT
 501  CATTGGCAAC CGACTTGGGA TCGATTTTCA ATTTCCCGAG GAGTTGTATT
 551  CATTCGATAG CGGTAAAGCG AAAAAGGCTT CCGGCAAGCC GCTTGCTCCA
 601  AGCTTGGCCG AAGCGGTGGC AGGGCTCGGT CCCGCTGCAA GTGATAAGGA
 651  TGCGCTAGTT CCGTACGCGA GCTCGGAACC TGTCAATGCA TTCGATGCCC
 701  GAATGCGGGC GGGAAATCGC GTCGAGGTGG TAACTCACCA CGTTCGAGTC
 751  GAGGCTGCGG AGCGTATGCA GGTTGAACTG CTCAAACCGG GTCAGACGAT
 801  GAAAGACCTG CCGCCCGAGC TTTGTCATGA GAGCTACAGG CGGCGAGCAA
 851  ACCGGCGAGT ATCGGACGGT ACGCCAACCG AGAAGCGGGG CGGCGCGCCT
 901  TCAGGGATCA AACGTCTGCA TGGCAATCTG CAGAGCCTCA CGATCACGGG
 951  GCCTGCTGCT CGGGAATTTA TTCATCCTAC AGAGCATCGT CCTTTGACCA
1001  TTCGCGAGTG TGCCCGCATT CAGACATTTC CCGACAAGTA CAGGTGGGTT
1051  GGCAACAATG CCAGCGTCAT TCAGCAAATT GGAAACGCTG TGCCACCGCT
1101  CGCTGCTGAA CGTTTGGCCA AACACTTAAG AGATATTGAT GGGTCGTTTG
1151  GTGCAGATAC GCGACCGGCA GGTGCGATGT CTGCAAAGCT ATTAGGATTT
1201  GTTCTTACTG AAGCGCTTGG AATGAGTCCG GCACTCAAAT CAACAGAAGC
1251  GCTGCTTGCA GAAATGCACC AAGGGGGATT CGTTTTTTAA
```

FIG. 2

ApaLI endonuclease gene sequence

```
   1  ATGACTACAC GGCAACGACT CAGCGCAGAG CGATCGCAGC AGCTCACTCG
  51  CCTGCTTACG ATCACGAAGA CAGCAAACAT GCGGGCGCTC ATGGAGGCCA
 101  GCGAGCTAGC CAAAGTAATT GCACTTGTGG CCGTTGACAT CGGCAAGAGT
 151  GATGAAATGG CGCGAGCATT TCCTGTGCTC TGGCCGAAAA TTTCTCCGCA
 201  ACAGGAGTAC TACGCCACGG CAGTTGACTG GTTCACCAAC CCCGACGAGA
 251  CGGTTACGTC CTTTGATGTT GTCGATATGC TTGATGCAGG CACGTCACTG
 301  GATCAGGACT TCATGACCTA TCTGAAATGC CTCACCGAGC TTCATAAGCG
 351  CCGTCGTAAA TATGGATTGA TTCTTCAGAG GCAGCCTCTG CCGACTATGG
 401  TCCAAGTCTC CCCTAGGGCG CTCATGGAAT ACGGCCCTGA CTTTCCGCCG
 451  GAAGCACTTG CTTCATGGCT CACTTGGCGC AAATTCTTTT ACGATTTGGA
 501  CAATCGGTCT GCACAGGAAA CCGGCTATCT TTTCGAACCC ATCCTTGCTG
 551  CAGCCATCGG CGGTGAGGCG AAGTCGGCGC GGGAGCGTGT GGTGAGGCGC
 601  ACTGATGACC CTACTAAGGG TCGGCAAGTC GACTGCTGGA AAGTGCTGCC
 651  GGACGGAACT CCACTTGCGT ACGAATTGAA GTTGCGCGTG ACGATTGCGG
 701  CTAGCGGGCA AGGGCGTTTT GGCGAGGAGC TCTCATTTGC TCGCGACTGC
 751  AGTAGTTCGG GTGCAAAGCC AATTCTTGTT GTGCTGGATC CCACAGAAAA
 801  TGACAAACTG ACCGGGCTTC AGGCCGCGTA CCGAGAGGTG GGCGGCGCCG
 851  CTTATGTGGG CGATGCGGCT TGGGCTCACC TCGAAGACGA GGCGGGGGCA
 901  ACGATGGCAT CGTTTATTGA ACGCTATGTT CGCGTGCCGG TGGCTTCTGT
 951  GTCCAGCTTT GAGCGGGTTA TCGAGGGTGA CGCAACCAAG CGTAGTCTCA
1001  TCTTGCAGGA CCTGCAGGCA CGGCTTGATG GCAATGAACT GACAATCTCG
1051  CTTGGTGGCC ATCAACGCTT GGTCGAGCGT CATGAAGATC AGAGTTTGGC
1101  TGCCGATGGG GATGATGACA GCGAATAG
```

FIG. 3

CLONING AND EXPRESSION OF THE APALI RESTRICTION ENDONUCLEASE

BACKGROUND OF THE INVENTION

The present invention relates to recombinant DNA which encodes the ApaLI restriction endonuclease and modification methylase, and the production of ApaLI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the "recognition sequence") along with the DNA molecule. Once bound, they cleave the molecule within, or to one side of, the recognition sequence. Different restriction endonucleases have affinity for different recognition sequences. Over one hundred and ninety restriction endonucleases with unique specificities have been identified among the many hundred of bacterial species that have been examined to-date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the DNA sequences TTTAAA (SEQ ID NO:1), PuGGNCCPy (SEQ ID NOP:2) and CACNNNGTG (SEQ ID NO:3), respectively. *Escherichia coli* TY13, on the other hand, synthesizes only one enzyme, EcoRI, which recognizes the DNA sequence GAATTC (SEQ ID NO:4).

It is thought that in nature, restriction endonucleases play a protective role in the welfare of the bacterial cell. They enable bacteria to resist invasion by viruses and foreign DNA. They impart this resist by cleaving the DNA of the invading organism. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or more of the nucleotides within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonucleases. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in great quantities. The key to cloning restriction endonuclease genes is to develop a simple and reliable method to identify such clones within complex "libraries", i.e., populations of clones derived by "shotgun" procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcORII:Koshyh, et al., *Molec. Gen. Genet.* 178:717–719 (1980); HhaII:Mann, et al., *Gene* 3:97–112 (1978); PstI:Walder, et al., *Proc. Nat. Acad. Sci. USA* 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been shown that cloned restriction-modification genes do not always manifest sufficient phage resistance to confer selective survival.

Another cloning approach involves transferring systems initially characterized as plasmid-borne into *E. coli* cloning plasmids (EcoRV:Bougueleret, et al., *Nucl. Acid Res.* 12:3659–3676 (1984); PaeR7:Gingeras and Brooks, *Proc. Nat. Acad. Sci. USA* 80:402–406 (1983); Theriault and Roy, *Gene* 19:355–359 (1982): PvuII:Blumenthal, et al., *J. Bacteriol.* 164:501–509 (1985)).

A third approach, being used to clone a growing number of R-M systems, is by selection for an active methylase gene (refer to EPO No. 193 413 published Sep. 3, 1986 and BsuRI:Kiss, et al., *Nucl. Acad Res.* 13:6403–6421 (1985)). Since restriction and modification genes are often closely linked, both genes 10 can often be cloned simultaneously. This selection does not always yield a complete restriction system, however, but instead yields only the methylase gene (BspRI:Szomolanyi, et al., *Gene* 10:219–225 (1980); BcnI:Janulaitis, et al., *Gene* 20:197–204 (1982); BsuRI:Kiss and Baldauf, *Gene* 21:111–119 (1983); and MspI:Walder, et al., *J. Biol. Chem.* 258:1235–1241 (1983)).

A more recent method (the "Endo-Blue" method) has been described for direct cloning of restriction endonuclease genes using an indicator strain of *E. coli* containing a dinD::lacZ fusion. This method utilizes the *E. coli* SOS response following DNA damages by endonuclease or non-specific nucleases. A number of thermostable nuclease genes (BsoBI, TaqI, Tth111I, Tf nuclease) have been cloned using this method (Fomenkov, et al., *Nucl. Acid Res.* 22:2399–2403 (1994)).

Another obstacle to cloning these genes in *E. coli* was discovered in the process of cloning diverse methylases. Many *E. coli* strains (including those normally used in cloning) have methylation-dependent restriction systems (McrA, McrBC and Mrr) that resist the introduction of DNA containing methylated cytosine or adenine bases (Raleigh and Wilson, *Proc. Nat. Acad. Sci. USA* 83:9070–9074 (1986); Heitman and Model, *J. Bact.* 169:3243–3250 (1987)). Therefore, it is also necessary to carefully consider which *E. coli* strain(s) to use for cloning methylase genes.

Because purified restriction endonucleases, and to a lesser extent, modification methylases, are useful tools for characterizing genes in the laboratory, there is a commercial incentive to obtain bacterial strains through recombinant DNA techniques that synthesizes these enzymes in abundance. Such strains would be useful because they would simplify the task of purification, as well as providing the means for production of these enzymes in commercially useful amounts.

SUMMARY OF THE INVENTION

The present invention relates to a method of cloning ApaLI methylase gene (apaLIM) and ApaLI endonuclease gene (apaLIR) from *Acetobacter pasteurianus* into *E. coli* by the methylase selection method and inverse PCR. The ApaLI methylase gene was cloned into pUC19 (3 ApaLI sites inserted) by the methylase selection method. Eight ApaLI-resistant clones were isolated and found to contain apaLIM gene. However, these clones are not stable such that sometimes overnight cultures were lysed or plasmid DNA was lost in the unlysed culture.

Fresh transformation was required to maintain the clone using the original DNA isolate. Further mapping indicated that instability was caused by a gene product(s) of about 1.1 kb DNA fragment adjacent to the apaLIM gene. It was reasoned that this "toxic" region may encode part or all of the ApaLI endonuclease. The cell lysates of these ApaLI-resistant clones were analyzed for ApaLI endonuclease activity. However, no apparent ApaLI endonuclease activity was detected in the cell extract. Nevertheless, an SOS response was induced as evidenced by blue colony formation when plasmids containing this "toxic" region were used to transform dinD::lacZ indicator strain and plated in X-gal plates. From these results it was speculated that the "toxic" region may be part of the apaLIR gene and that the truncated form of ApaLI endonuclease is toxic to *E. coli* cells even in the presence of ApaLI methylase. Further efforts were made to clone and sequence DNA fragments adjacent to the methylase gene. One unfinished open reading frame (ORF) was found following the apaLIM gene. The adjacent DNA was cloned by inverse PCR and sequenced. It was found that the ORF contains an additional twelve codons before the stop codon. The entire ORF was cloned by amplifying the DNA with PCR from genomic DNA and inserted into pRRS expression vector. ApaLI endonuclease activity was detected in the cell lysate when *E. coli* cells carrying this plasmid were induced with IPTG. Thus, it was confirmed that the ORF immediately following the apaLIM gene is the apaLIR gene. The apaLIM and apaLIR genes are organized in the same direction. These two genes overlap by 1 bp (the last base in the TAA stop codon of apaLIM gene was used as the first base in the ATG start codon of the apaLIR gene).

BRIEF DESCRIPTION OF THE DRAWINGS

FIG. 2 is the DNA sequence (SEQ ID NO:5) of apaLIM gene and its encoded protein sequence.

FIG. 3 is the DNA sequence (SEQ ID NO:6) of apaLIR gene and its encoded protein sequence.

DETAILED DESCRIPTION OF THE INVENTION

Figure 1:
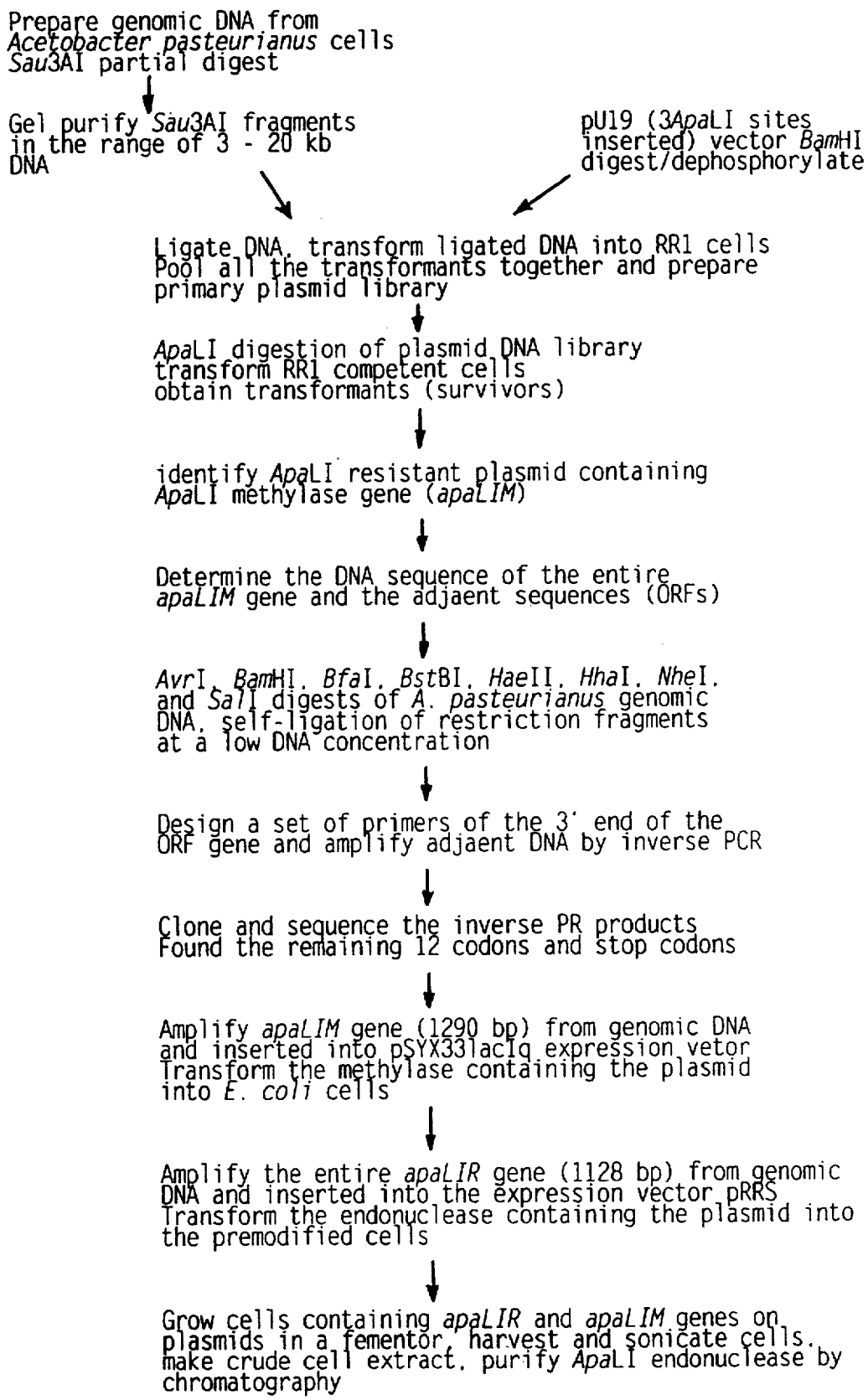
FIG. 1 is a scheme for cloning and producing the ApaLI restriction endonuclease.
Figure 1:
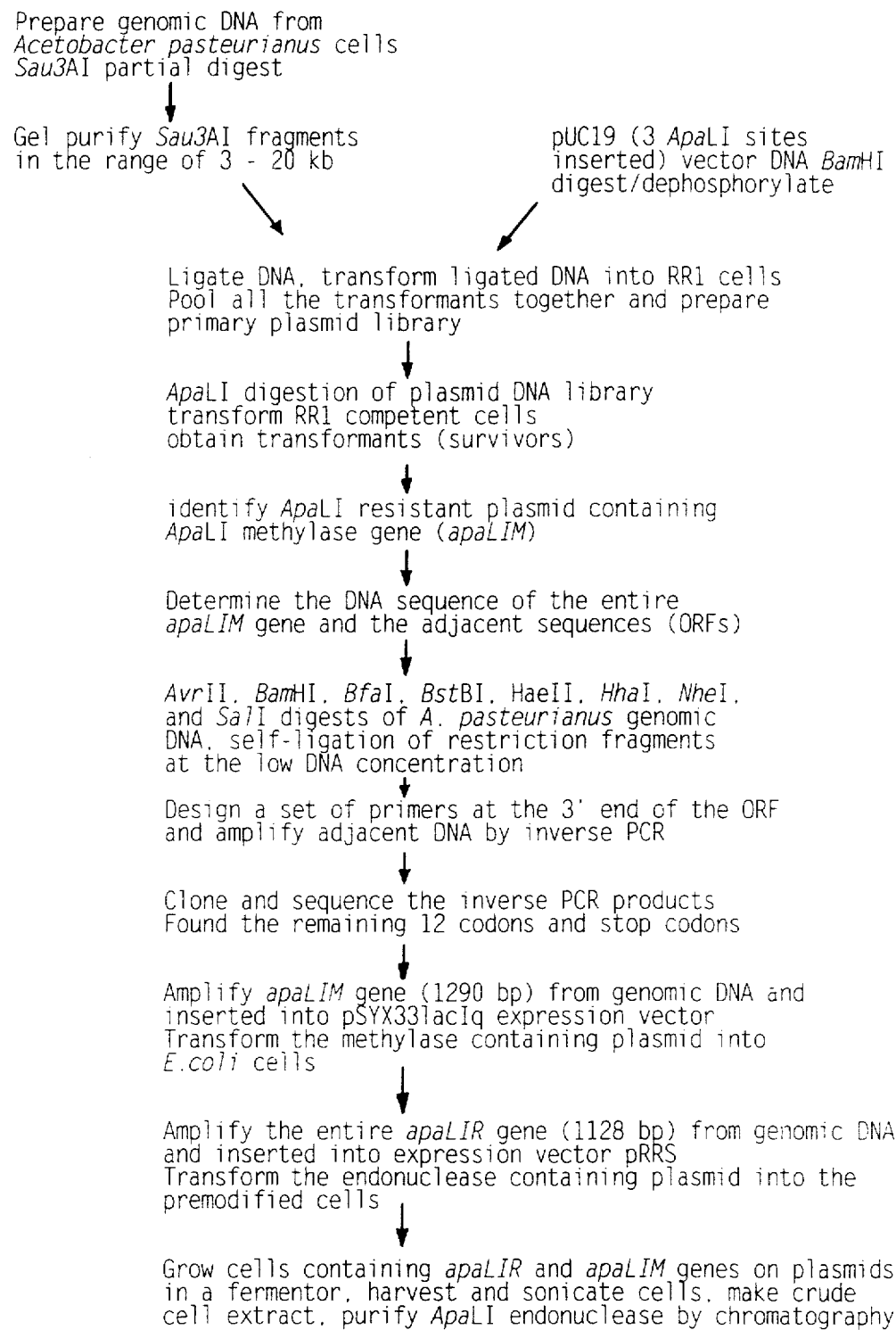

The method described herein by which the apaLIM and apaLIR genes are cloned and expressed is illustrated in FIG. 1 and includes the following steps:

1. The genomic DNA of *Acetobacter pasteurianus* (ATCC No. 12875) is purified.
2. The DNA is digested partially with a restriction endonuclease such as Sau3AI, or any of its isoschizomers, that generates DNA fragments (3 to 20 kb) containing the entire apaLIM and/or apaLIR gene. Alternatively, one could made a library which contains the entire restriction-modification system such as ApaI, BclI, BglI, BglII, BsaWI, BspEI, EagI, EcoRI, EcoRV, Pfl1108I, StuI, or SspI genomic library. The fragment (s) should also be of cloneable size, that is, between 2.6–20 kb.
3. The Sau3AI-digested genomic DNA fragments are ligated into BamHI-cleaved/CIP treated pUC19 cloning vector (this vector contains three ApaLI sites for selection). The ligation mixture is used to transform an appropriate host, i.e., a hsdR$^-$, mcrBC$^-$, mrr$^-$ strain, such as *E. coli* strain RR1. The DNA/cell mixtures are plated on ampicillin (Ap) selective media for transformed cells. After incubation, the transformed cells are pooled together to form the primary cell library.
4. The recombinant plasmids are purified in toto from the primary cell library to make primary plasmid library. The purified plasmid library is then digested to completion in vitro with ApaLI endonuclease, or any ApaLI isoschizomer. ApaLI endonuclease digestion causes the selective destruction of unmodified, non-methylase-containing clones, resulting in an increase in the relative frequency of ApaLI methylase-carrying clones.
5. Identification of ApaLI methylase clone: The digested plasmid library DNA is transformed back into a host such as *E. coli* strain RR1 and transformed colonies are again obtained by plating on Ap plates. The colonies are picked and their plasmid DNA was prepared and analyzed for the presence of the ApaLI methylase gene by incubating purified plasmid DNA in vitro with ApaLI endonuclease to determine whether it is resistant to ApaLI digestion.
6. Once it has been established that the methylase gene has been cloned, the clone is analyzed by restriction mapping and deletion mapping. Since the original isolate was not stable, subclone and deletion clones are constructed and the entire apaLIM is sequenced. The adjacent DNA on both sides of the apaLIM gene is also sequenced. When following the above outlined protocol, open reading frames (ORF) were identified on all six coding frames and compared to all gene sequences in GenBank. One ORF (582 bp) was found to proceed the apaLIM gene, which has 56% identity with a DNA invertase from *Shigella boydii*. One unfinished ORF (no stop codon has yet been identified) was found following the apaLIM gene. This unfinished ORF shows no significant homology with any genes in GenBank, suggesting this is a new gene that has not been identified before. Most likely, this ORF may encode the ApaLI endonuclease.
7. One set of primers were designed which annealed to the end of the unfinished ORF. Inverse PCR is used to amplify the remaining DNA sequence from *A. pasteurianus* genomic DNA that has been cleaved with AvrII, BamHI, BraI, BstBI, HaeII, HhaI, NheI or SalI and self-ligated at a low DNA concentration.
8. Inverse PCR products are amplified from BamHI, HaeII, and NheI cleaved/self-ligated genomic DNA templates. The DNA is treated with T4 polynucleotide kinase and DNA polymerase and cloned into HincII-cleaved/CIP treated pUC19 vector. The inserts are sequenced and the DNA sequences translated into amino acid sequences in all six reading frames. Thirteen remaining codons (12 codons encoding amino acids and one stop codon) are found for the unfinished ORF. The entire ORF is 1128 bp, coding for a 375 amino acid protein with predicted molecular weight of 41.7 kDa.
9. To confirm the 1128-bp ORF is the apaLIR gene, the apaLIM gene is first cloned into a pSC101 derivative (pSX331aqIq, Kan$^R$) to premodify *E. coli* host. The entire ORF is amplified by PCR with two primers. The forward primer contains the ribosome binding site and 6 bp spacing before the ATG start codon. The PCR DNA is cloned into an expression vector pRRS and transformed into ApaLI methylase premodified cells.

10. Cells harboring pSX331aqIq-ApaLIM⁺ and pRRS-ORF were induced with IPTG. Induced cells are lysed with lysozyme treatment and sonication. ApaLI endonuclease activity was found when crude cell lysates were prepared and assayed for activity on λDNA substrate. To make large amounts of ApaLI endonuclease, cells containing both the apaLIM and apaLIR genes on plasmids are grown in a 100 liter fermentor to late log phase and induced with IPTG overnight. ApaLI endonuclease is purified by chromatography.

The following Example is given to illustrate embodiments of the present invention as it is presently preferred to practice. It will be understood that this Example is illustrative, and that the invention is not to be considered as restricted thereto except as indicated in the appended claims.

EXAMPLE I

CLONING OF ApaLI RESTRICTION-MODIFICATION SYSTEM

1. Cloning of apaLIM Gene In pUC19

Sau3AI genomic DNA library was constructed using pUC19 (three ApaLI sites inserted in the SmaI, SspI, and DraI sites of pUC19, respectively) as a cloning vector as follows:*A. pasteurianus* genomic DNA was digested partially with Sau3AI and the digested DNA was resolved in an agarose gel. DNA fragments in the range of 3 to 20 kb were gel-purified. The gel slices were frozen and thawed twice and spun in a microcentrifuge for 15 min. at 14 k/min. DNA was precipitated with 95% ethanol and 0.3 M NaAc salt and washed with 70% ethanol. The DNA pellet was dried under vacuum and resuspended in TE buffer to make a final concentration of 0.5 mg/ml. The gel-purified genomic DNA was ligated to BamHI cleaved/CIP treated pUC19. Ligated DNA mixture was transformed into RR1 competent cells and plated on Ap plates using the standard transformation procedure. A total of approximately 8×10³ transformants were obtained. All the colonies were harvested and inoculated into 500 ml of LB medium plus Ap and cells were cultured overnight at 37° C. Plasmid DNA was prepared from the overnight cells following the purification procedure of Qiagen maxi-prep column. 0.1 μg, 0.25 μg, 0.5 μg and 1 μg of the plasmid DNA library were challenged with 100 units of ApaLI endonuclease in a 100 μl volume in 1x ApaLI reaction buffer (50 mM KAc, 20 mM Tris-acetate, 10 mMMgAc2, 1 mM DTT, 100 μg/ml BSA) at 37° C. for two hours. The ApaLI-digested DNA was used to retransform Pal competent cells and plated on Ap plates. Plasmid DNA was isolated again from the surviving transformants and digested with ApaLI restriction enzyme to see if the plasmid DNA is resistant to ApaLI digestion. A total of 106 plasmids were checked for resistance to ApaLI digestion. Eight isolates were found to be resistant. All eight isolates share a common 830-bp (approximate size) EcoRI/HindIII fragment. Presumably, this common fragment is part of the apaLIM gene. When the cells carrying the 8 resistant plasmids were cultured overnight in 500 ml large culture, the cells in four cultures were lysed. The cells in the remaining four cultures were harvested and resuspended in a sonication buffer (10 mM Tris-HCl, pH 8, 10 mM β-mercaptoethanol). Cells were lysed by lysozyme treatment and sonication. No ApaLI endonuclease activity was found in the cell extracts of the four remaining clones on λDNA substrate. #19 isolate seems to contain the largest insert (about 6 kb) among the eight clones. Therefore #19 was chosen to be characterized further. In order to prepare #19 plasmid DNA, fresh transformants were obtained everytime before plasmid DNA preparation. The yield of plasmid DNA was extremely low compared to the high copy number vector DNA, indicating that #19 plasmid carries a "toxic" region in the insert. Consistent with the above conclusion, when #19 plasmid DNA was used to transform *E. coli* cells, one natural deletion was found among 12 transformants. This natural deletion occurred in the region that includes the common EcoRI/HindIII fragment and downstream of this fragment. In order to maintain the plasmid clone, several restriction fragment deletion clones were constructed. It was found that one AvrII site was located within the "toxic" region. A 5.4 kb deletion (AvrII/SphII fragment deletion) inactivated the "toxic" gene effect and alleviate the copy number problem. Further mapping indicated that one AflII site is located outside of the "toxic" region. A deletion clone that deleted out the AflII/SphI fragment (4.8 kb) is still unstable and the plasmid has a low copy number. The toxic region has been narrowed down to within a 1.2 kb fragment. A 2.5 kb EcoRI fragment deletion that deleted this 1.2 kb region also removed the toxic effects. The entire methylase gene and the DNA on both sides of the apaLIM gene were sequenced by the Sanger's dideoxy-termination method. A total of 5388 bp DNA sequence were obtained from subclones of #19 isolate. The new DNA sequence was compared to the DNA sequences in GenBank to see any homology. It was found that ApaLI methylase has extensive homology with other C5 methylases. The predicted amino acids from one ORF (582 bp) proceeding the methylase gene have 56% identity with a DNA invertase from *Shigella boydii*. One unfinished ORF (1089 bp) immediately following the apaLIM gene has no significant homology with any genes in the GenBank, suggesting this ORF is a new gene. No stop codon was found for this ORF, indicating this fragment is missing part of the gene.

2. Use of Inverse PCR to Clone the Remaining DNA

Inverse PCR is an efficient way to clone adjacent DNA to a known DNA sequence. *A. pasteurianus* genomic DNA was cleaved with AvrII, BamHI, BfaI, BstBI, HaeII, HhaI, NheI, or SalI and self-ligated at a low DNA concentration in a total volume of 500 μl (20 μl restricted genomic DNA, about 2 μg, 50 μl 10x ligation buffer, 5 μl T4 DNA ligase, 425 μl sterile distilled H₂O) at 16° C. overnight. The ligated DNA was extracted once with Phenol-CHCl₃, and once with CHCl₃ and precipitated with 95% ethanol, washed with 70% ethanol and dried. The DNA was used as templates for inverse PCR reaction (95° C. 1 min., 55° C. 1 min., 72° C. 5 min., 30 cycles). One set of primers that annealed to the end of the ORF was designed as follows: forward primer, 5'GGCATCGTTTATTGAACGCTATGT3' (SEQ ID NO:7), reverse primer, 5'CCCCCGCCTCGTCTTCGAGGTGAG3' (SEQ ID NO:8). A 700 bp, 850 bp, and 1400 bp products were found in the inverse PCR reactions, respectively using the self-ligated NheI, HaeII, and BamHI genomic DNA templates. The inverse PCR products were treated with T4 polynucleotide kinase and T4 DNA polymerase and cloned into HincII site of pUC19. The inserts were sequenced and the new sequence was translated in all six frames. Thirteen codons were found to be continuous from the ORF. Thus bringing the size of the ORF to 1128 bp, coding for a 375 amino acid protein with predicted molecular weight of 41.7 kDa.

3. Expression of ApaLI Endonuclease in *E. coli*

To confirm this ORF is the apaLIR gene, the apaLIM gene was first subcloned into a pSC101 derivative, pSX331lacI^q to premodify *E. coli* host. The apaLIM gene is constitutively expressed from the promoter of Tet^R gene. The laqI^q gene on this plasmid regulates the lac$^{UV5}$ promoter that is on the pRRS plasmid for the ORF expression. The entire ORF was amplified by PCR with two primers. The forward primer contains the ribosome binding site and 6 bp spacing before the ATG start codon (forward primer, 5'AGGAAGCTTG-GAGGTTTAAAA<u>ATG</u>ACTACACGGCAA CGACT-CAGC3' (SEQ ID NO:9); reverse primer, 5'GCCG CATG-CAACCTATTCGCTGTCATCATCCCC3' (SEQ ID NO:10)). The PCR product was cleaved with HindIII and SphI endonucleases, cloned into expression vector pRRS and transformed into ApaLI methylase premodified cells (*E. coli* ER2428 having the pSX331aqIq-ApaLIM$^+$ plasmid). Transformants were plated on Ap and Km plates. *E. coli* cells of 500 ml culture carrying pRRS-ORF and pSX331aqIq-ApaLIM$^+$ were grown to 120 klett units at 30° C. in LB plus Ap (100 μg/ml) and Km (50 μg/ml) and the ORF expression was induced for 4 hours by addition of IPTG to 0.5 mM. Cells were harvested and resuspended in 30 ml of sonication buffer. Cell lysis was completed by addition of lysozyme to 100 μg/ml and sonication. Cell debris was removed by centrifugation at 15 k/min. The cell extract was diluted 10-, 100-, 1,000-, and 10,000-fold in TE buffer. 5 μl of the diluted extract was used to digest 1 μg λDNA for 1 hour at 37° C. The digested DNA was resolved in a 0.8% agarose gel. It was found that the clone makes $1\times10^6$ units of ApaLI endonuclease/gram of wet *E. coli* cells. The expression result confirmed that the ORF immediately following the apaLIM gene is the apaLIR gene. Both genes overlap by 1 base. That is, the last base A in the TAA stop codon in the apaLIM gene is used as the first base A in the ATG start codon of the apaLIR gene.

A sample of the ER2428 containing both pRRS-ApaLIR$^+$ and pSX331aqIq-ApaLIM$^+$ (NEB#962) has been deposited with the American Type Culture Collection on May 23, 1995 and received ATCC Accession Number 69824.

What is claimed is:

1. Isolated DNA coding for the ApaLI restriction endonuclease, wherein the isolated DNA is obtainable from *Acetobacter pasteurianus*.

2. A recombinant DNA vector comprising a vector into which a DNA segment coding for the ApaLI restriction endonuclease has been inserted.

3. Isolated DNA coding for the ApaLI restriction endonuclease and methylase, wherein the isolated DNA is obtainable from ATCC No. 69824.

4. A cloning vector which comprises the isolated DNA of claim 3.

5. The cloning vector of claim 4, wherein the cloning vector comprises pRRS-ApaLIR$^+$.

6. A host cell transformed by the cloning vector of claim 2, 4, or 5.

7. A method of producing an ApaLI restriction endonuclease comprising culturing a host cell transformed with the vector of claim 2, 4, or 5 under conditions suitable for expression of said endonuclease.

\* \* \* \* \*

UNITED STATES PATENT AND TRADEMARK OFFICE
CERTIFICATE OF CORRECTION

PATENT NO. : 5,616,484                  Page 1 of 15

DATED : April 1, 1997

INVENTOR(S) : Xu

It is certified that error appears in the above-indentified patent and that said Letters Patent is hereby corrected as shown below:

IN THE FIGURES

Replace Figure 1 with new Figure 1, as shown on the following page.

Column 1, line 32, replace "SEQ ID NOP:2" with --SEQ ID NO:2--

Column 3, line 47, delete "and its encoded protein sequence"

Column 3, line 49, delete "and its encoded protein sequence"

Column 7, line 15, replace "klett" with --Klett--

UNITED STATES PATENT AND TRADEMARK OFFICE
CERTIFICATE OF CORRECTION

PATENT NO. : 5,616,484　　　　　　　　　　　　　Page 3 of 15

DATED : April 1, 1997

INVENTOR(S) : Xu

It is certified that error appears in the above-indentified patent and that said Letters Patent is hereby corrected as shown below:

IN THE ABSTRACT

Line 1, replace "ApaLI" with --*ApaL*I--

Line 2, replace "apaLIM" with --*apaLIM*--

Line 2, replace "ApaLI" with --*ApaL*I--.

Line 3, replace "apaLIR" with --*apaLIR*--

Line 4, replace "ApaLI" with --*ApaL*I--

Line 5, replace "ApaLI" with --*ApaL*I--

Line 6, replace "ApaLI" with --*ApaL*I--

Line 7, replace "apaLIM" with --*apaLIM*--

Column 1, line 7, replace "ApaLI" with --*ApaL*I--

Column 1, line 8, replace "ApaLI" with --*ApaL*I--

Column 1, line 30, replace "DraI, DraII and DraIII" with
--*Dra*I, *Dra*II and *Dra*III--

UNITED STATES PATENT AND TRADEMARK OFFICE
CERTIFICATE OF CORRECTION

PATENT NO. : 5,616,484  Page 4 of 15

DATED : April 1, 1997

INVENTOR(S) : Xu

It is certified that error appears in the above-indentified patent and that said Letters Patent is hereby corrected as shown below:

Column 1, line 34, replace "EcoRI" with --*Eco*RI--

Column 2, line 7, replace "EcORII" with --*Eco*RII--

Column 2, line 8, replace "HhaII" with --*Hha*II--

Column 2, line 9, replace "PstI" with --*Pst*I--

Column 2, line 20, replace "EcoRV" with --*Eco*RV--

Column 2, line 21, replace "PaeR7" with --*Pae*R7--

Column 2, line 23, replace "PvuII" with --*Pvu*II--

Column 2, line 28, replace "BsuRI" with --*Bsu*RI--

Column 2, line 30, delete "10"

Column 2, line 33, replace "BspRI" with --*Bsp*RI--

Column 2, line 33, replace "BcnI" with --*Bcn*I--

Column 2, line 34, replace "BsuRI" with --*Bsu*RI--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 2, line 35, replace "MspI" with --*Msp*I--

Column 2, line 40, replace "dinD::lacZ" with --*dinD::lacZ*--

Column 2, line 43, replace "BsoBI, TaqI, Tth111I, Tf" with --*Bso*BI, *Taq*I, *Tth*111I, *Tf*--

Column 2, line 49, replace "McrA, McrBC and Mrr" with --*Mcr*A, *Mcr*BC and *Mrr*--

Column 2, last line, replace "ApaLI" with --*Apa*LI--

Column 2, last line, replace "apaLIM" with --*apaL*IM--

Column 2, last line, replace "ApaLI" with --*Apa*LI--

Column 3, line 1, replace "apaLIR" with --*apaL*IR--

Column 3, line 3, replace "ApaLI" with --*Apa*LI--

Column 3, line 3, replace "ApaLI" with --*Apa*LI--

Column 3, line 5, replace "ApaLI" with --*Apa*LI--

Column 3, line 6, replace "apaLIM" with --*apaL*IM--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 3, line 12, replace "apaLIM" with --*apaLIM*--

Column 3, line 14, replace "ApaLI" with --*ApaL*I--

Column 3, line 15, replace "ApaLI" with --*ApaL*I--

Column 3, line 16, replace "ApaLI" with --*ApaL*I--

Column 3, line 20, replace "dinD::lacZ" with --*dinD::lacZ*--

Column 3, line 22, replace "apaLI" with --*apaLIR*--

Column 3, line 23, replace "ApaLI" with --*ApaL*I--

Column 3, line 24, replace "ApaLI" with --*ApaL*I--

Column 3, line 27, replace "apaLIM" with --*apaLIM*--

Column 3, line 32, replace "ApaLI" with --*ApaL*I--

Column 3, line 35, replace "apaLIM" with --*apaLIM*--

Column 3, line 35, replace "apaLIR" with --*apaLIR*--

Column 3, line 36, replace "apaLIM" with --*apaLIM*--

Column 3, line 36, replace "apaLIR" with --*apaLIR*--

UNITED STATES PATENT AND TRADEMARK OFFICE
CERTIFICATE OF CORRECTION

PATENT NO. : 5,616,484

DATED : April 1, 1997

INVENTOR(S) : Xu

Page 7 of 15

It is certified that error appears in the above-indentified patent and that said Letters Patent is hereby corrected as shown below:

Column 3, line 38, replace "apaLIM" with --*apaLIM*--

Column 3, line 39, replace "apaLIR" with --*apaLIR*--

Column 3, line 43, replace "ApaLI" with --*ApaL*I--

Column 3, line 45, replace "apaLIM" with --*apaLIM*--

Column 3, line 47, replace "apaLIR" with --*apaLIR*--

Column 3, line 54, replace "apaLIM" with --*apaLIM*--

Column 3, line 55, replace "apaLIR" with --*apaLIR*--

Column 3, line 60, replace "Sau3AI" with --*Sau3A*I--

Column 3, line 62, replace "apaLIM" with --*apaLIM*--

Column 3, line 62, replace "apaLIR" with --*apaLIR*--

Column 3, line 64, replace "ApaI" with --*Apa*I--

Column 3, line 64, replace "BclI" with --*Bcl*I--

Column 3, line 64, replace "BglI" with --*Bgl*I--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 3, line 64, replace "BgIII" with --*Bg*lII--

Column 3, line 65, replace "BsaWI, BspEI, EagI, EcoRI, EcoRV, PflI108I, StuI" with --*Bsa*WI, *Bsp*EI, *Eag*I, *Eco*RI, *Eco*RV, *Pfl*1108I, *Stu*I--

Column 3, line 66, replace "SspI" with --*Ssp*I--

Column 4, line 1, replace "Sau3AI" with --*Sau*3AI--

Column 4, line 2, replace "BamHI" with --*Bam*HI--

Column 4, line 3, replace "ApaLI" with --*Apa*LI--

Column 4, line 10, replace "in toto" with --*in toto*--

Column 4, line 12-13, replace "in vitro" with --*in vitro*--

Column 4, line 13, replace "ApaLI" with --*Apa*LI--

Column 4, line 13, replace "ApaLI" with --*Apa*LI--

UNITED STATES PATENT AND TRADEMARK OFFICE
CERTIFICATE OF CORRECTION

PATENT NO. : 5,616,484
DATED : April 1, 1997
INVENTOR(S) : Xu

It is certified that error appears in the above-indentified patent and that said Letters Patent is hereby corrected as shown below:

Column 4, line 14, replace "ApaLI" with --*Apa*LI--

Column 4, line 17, replace "ApaLI" with --*Apa*LI--

Column 4, line 18, replace "ApaLI" with --*Apa*LI--

Column 4, line 23, replace "ApaLI" with --*Apa*LI--

Column 4, line 24, replace "in vitro" with --*in vitro*--

Column 4, line 24, replace "ApaLI" with --*Apa*LI--

Column 4, line 25, replace "ApaLI" with --*Apa*LI--

Column 4, line 30, replace "apaLIM" with --*apaL*IM--

Column 4, line 31, replace "apaLIM" with --*apaL*IM--

Column 4, line 35, replace "apaLIM" with --*apaL*IM--

Column 4, line 38, replace "apaLIM" with --*apaL*IM--

Column 4, line 42, replace "ApaLI" with --*Apa*LI--

Column 4, line 46, replace "AvrII, BamHI" with --*Avr*II, *Bam*HI--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 4, line 47, replace "Brai, BstBI, HaeII, HhaI, NheI or SalI" with --*Bfa*I, *Bst*BI, *Hae*II, *Hha*I, *Nhe*I or *Sal*I--

Column 4, line 49, replace "BamHI" with --*Bam*HI--

Column 4, line 49, replace "HaeII" with --*Hae*II--

Column 4, line 50, replace "NheI" with --*Nhe*I--

Column 4, line 52, replace "HincII" with --*Hinc*II--

Column 4, line 60, replace "apaLIR" with --*apaLIR*--

Column 4, line 61, replace "apaLIM" with --*apaLIM*--

Column 4, line 62, replace "pSX33laqIq" with --pSX33laqI$^q$--

Column 4, last line, replace "ApaLI" with --*Apa*LI--

Column 5, line 1, replace "pSX33laqIq" with --pSX33laqI$^q$--

Column 5, line 3, replace "ApaLI" with --*Apa*LI--

Column 5, line 6, replace "ApaLI" with --*Apa*LI--

Column 5, line 7, replace "apaLIM" with --*apaLIM*--

UNITED STATES PATENT AND TRADEMARK OFFICE
CERTIFICATE OF CORRECTION

PATENT NO. : 5,616,484

DATED : April 1, 1997

INVENTOR(S) : Xu

Page 11 of 15

It is certified that error appears in the above-indentified patent and that said Letters Patent is hereby corrected as shown below:

Column 5, line 7, replace "apaLIR" with --*apaL IR*--

Column 5, line 9, replace "ApaLl" with --*Apa*Ll--

Column 5, line 22, replace "apaLIM" with --*apaL IM*--

Column 5, line 23, replace "Sau3AI" with --*Sau*3AI--

Column 5, line 24, replace "ApaLl" with --*Apa*Ll--

Column 5, line 24, replace "Smal, Sspl" with --*Sma*l, *Ssp*l--

Column 5, line 25, replace "Dral" with --*Dra*l--

Column 5, line 27, replace "Sau3AI" with --*Sau*3AI--

Column 5, line 35, replace "BamHI" with --*Bam*HI--

Column 5, line 45, replace "ApaLl" with --*Apa*Ll--

Column 5, line 45, replace "ApaLl" with --*Apa*Ll--

Column 5, line 47, replace "mMMgAc2" with --mM $MgAc_2$--

Column 5, line 48, replace "ApaLl" with --*Apa*Ll--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 5, line 49, replace "PaI" with --RR1--

Column 5, line 51, replace "ApaLI" with --*Apa*LI--

Column 5, line 52, replace "ApaLI" with --*Apa*LI--

Column 5, line 53, replace "ApaLI" with --*Apa*LI--

Column 5, line 55, replace "EcoRI/HindIII" with --*Eco*RI/*Hind*III--

Column 5, line 57, replace "apaLIM" with --*apaLIM*--

Column 5, line 63, replace "ApaLI" with --*Apa*LI--

Column 6, line 5, replace "Consistent" with --In consistent--

Column 6, line 9, replace "EcoRI/HindIII" with --*Eco*RI/*Hind*III--

Column 6, line 12, replace "AvrII" with --*Avr*II--

Column 6, line 13, replace "AvrII/SphII" with --*Avr*II/*Sph*II--

Column 6, line 15, replace "AfIII" with --*Af*III--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 6, line 17, replace "AflII/SphI" with --*AflII/SphI*--

Column 6, line 19, replace "EcoRI" with --*Eco*RI--

Column 6, line 21, replace "apaLIM" with --*apaLIM*--

Column 6, line 26, replace "ApaLI" with --*Apa*LI--

Column 6, line 30, replace "apaLIM" with --*apaLIM*--

Column 6, line 38, replace "AvrII, BamHI, BfaI, BstBI, HaeII HhaI, NheI" with --*Avr*II, *Bam*HI, *Bfa*I, *Bst*BI, *Hae*II--

Column 6, line 39, replace "SalI" with --*Sal*I--

Column 6, line 53, replace "NheI, HaeII, and BamHI" with --*Nhe*I, *Hae*II and *Bam*HI--

Column 6, line 56, replace "HincII" with --*Hinc*II--

Column 6, line 62, replace "ApaLI" with --*Apa*LI--

Column 6, line 63, replace "apaLIR gene, the apaLIM" with --*apaLIR* gene, the *apaLIM*--

UNITED STATES PATENT AND TRADEMARK OFFICE
CERTIFICATE OF CORRECTION

PATENT NO. : 5,616,484

DATED : April 1, 1997

INVENTOR(S) : Xu

It is certified that error appears in the above-indentified patent and that said Letters Patent is hereby corrected as shown below:

Column 6, line 65, replace "apaLIM" with --*apaLIM*--

Column 7, line 1, replace "lac$^{UV5}$" with --lac$_{UV5}$--

Column 7, line 9, replace "HindIII" with --*Hind*III--

Column 7, line 10, replace "SphI" with --*Sph*I--

Column 7, line 11, replace "ApaLI" with --*Apa*LI--

Column 7, line 12, replace "pSX33laqlq" with --pSX33laqI$^q$--

Column 7, line 15, replace "pSX33laqlq" with --pSX33laqI$^q$--

Column 8, line 8, replace "ApaLI" with --*Apa*LI--

Column 8, line 10, replace "apaLIM gene is the apaLIR" with --*apaLIM* gene is the *apaLIR*--

Column 8, line 12, replace "apaLIM" with --*apaLIM*--

Column 8, line 12, replace "apaLIR" with --*apaLIR*--

Column 8, line 16, replace "pSX33laqlq" with --pSX33laqI$^q$--

UNITED STATES PATENT AND TRADEMARK OFFICE
CERTIFICATE OF CORRECTION

PATENT NO. : 5,616,484
DATED : April 1, 1997
INVENTOR(S) : Xu

It is certified that error appears in the above-indentified patent and that said Letters Patent is hereby corrected as shown below:

IN THE CLAIMS

Col. 13, line 19,
Claim 1, line 1, replace "ApaLI" with --*Apa*LI--

Col. 13, line 23,
Claim 2, line 2, replace "ApaLI" with --*Apa*LI--

Col. 13, line 25,
Claim 3, line 1, replace "ApaLI" with --*Apa*LI--

Col. 14, line 24,
Claim 7, line 1, replace "ApaLI" with --*Apa*LI--

Signed and Sealed this

Nineteenth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:1:

T T T A A A                                                                                       6

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

R G G N C C Y                                                                                     7

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

C A C N N N G T G                                                                                 9

( 2 ) INFORMATION FOR SEQ ID NO:4:

( i ) SEQUENCE CHARACTERISTICS:
        ( A ) LENGTH: 6 base pairs (B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

GAATTC                                                                              6

(2) INFORMATION FOR SEQ ID NO:5:

(i) SEQUENCE CHARACTERISTICS:
  (A) LENGTH: 1290 base pairs
  (B) TYPE: nucleic acid
  (C) STRANDEDNESS: unknown
  (D) TOPOLOGY: unknown (ii) MOLECULE TYPE: DNA (genomic)

(xi) SEQUENCE DESCRIPTION: SEQ ID NO:5:

| ATGAATAAGG | ACGAAGTTGT | TGTATCTCTG | TTTGCTGGGG | CTGGGGGATT | CTCCTCTGGC | 60 |
| TTTAGTCAGG | CTGGTCTGAA | GCCTTTATTT | GGTGCGGAAA | TTAACGCTGA | TGCCTGCCAG | 120 |
| ACTTACCAAG | AGAATGTCGG | CAGCCCCCTG | CACCAGCTTG | ATCTGAGCAC | GGTTGACCCA | 180 |
| TCTCATATTG | AAATGCTCAC | GGGTGGCAAA | AGGCCGTTCG | TCGTTATTGG | CGGGCCGCCG | 240 |
| TGCCAAGGCT | TTAGTACCGC | TGGTCCGCGC | AATTTTGCAG | ATCCTCGCAA | TCTGCTCATT | 300 |
| TTTAACTACT | TAAATATCGT | TGAGCGGCTT | TCGCCCCGT  | TGGCTCATTT | CGAAAATGTC | 360 |
| GAAGGACTTT | TGACGTCTGG | TGGGGGGCGG | GACCTTGCGC | GTCTGGTACG | AGAGTTTGTC | 420 |
| GACATGGGAT | ATTCGGTACG | GCTCCAAAAG | GTAAACCTAG | CCGCATATGG | CGTGCCACAA | 480 |
| ACGCGTAAGC | GGGTGCTAAT | CATTGGCAAC | CGACTTGGGA | TCGATTTTCA | ATTTCCCGAG | 540 |
| GAGTTGTATT | CATTCGATAG | CGGTAAAGCG | AAAAAGGCTT | CCGGCAAGCC | GCTTGCTCCA | 600 |
| AGCTTGGCCG | AAGCGGTGGC | AGGGCTCGGT | CCCGCTGCAA | GTGATAAGGA | TGCGCTAGTT | 660 |
| CCGTACGCGA | GCTCGGAACC | TGTCAATGCA | TTCGATGCCC | GAATGCGGGC | GGGAAATCGC | 720 |
| GTCGAGGTGG | TAACTCACCA | CGTTCGAGTC | GAGGCTGCGG | AGCGTATGCA | GGTTGAACTG | 780 |
| CTCAAACCGG | GTCAGACGAT | GAAAGACCTG | CCGCCCGAGC | TTTGTCATGA | GAGCTACAGG | 840 |
| CGGCGAGCAA | ACCGGCGAGT | ATCGGACGGT | ACGCCAACCG | AGAAGCGGGG | CGGCGCGCCT | 900 |
| TCAGGGATCA | AACGTCTGCA | TGGCAATCTG | CAGAGCCTCA | CGATCACGGG | GCCTGCTGCT | 960 |
| CGGGAATTTA | TTCATCCTAC | AGAGCATCGT | CCTTTGACCA | TTCGCGAGTG | TGCCCGCATT | 1020 |
| CAGACATTTC | CCGACAAGTA | CAGGTGGGTT | GGCAACAATG | CCAGCGTCAT | TCAGCAAATT | 1080 |
| GGAAACGCTG | TGCCACCGCT | CGCTGCTGAA | CGTTTGGCCA | AACACTTAAG | AGATATTGAT | 1140 |
| GGGTCGTTTG | GTGCAGATAC | GCGACCGGCA | GGTGCGATGT | CTGCAAAGCT | ATTAGGATTT | 1200 |
| GTTCTTACTG | AAGCGCTTGG | AATGAGTCCG | GCACTCAAAT | CAACAGAAGC | GCTGCTTGCA | 1260 |
| GAAATGCACC | AAGGGGGATT | CGTTTTTTAA |            |            |            | 1290 |

(2) INFORMATION FOR SEQ ID NO:6:

(i) SEQUENCE CHARACTERISTICS:
  (A) LENGTH: 1128 base pairs
  (B) TYPE: nucleic acid
  (C) STRANDEDNESS: unknown
  (D) TOPOLOGY: unknown (ii) MOLECULE TYPE: DNA (genomic)

(xi) SEQUENCE DESCRIPTION: SEQ ID NO:6:

-continued

| | | | | | | |
|---|---|---|---|---|---|---|
| ATGACTACAC | GGCAACGACT | CAGCGCAGAG | CGATCGCAGC | AGCTCACTCG | CCTGCTTACG | 60 |
| ATCACGAAGA | CAGCAAACAT | GCGGGCGCTC | ATGGAGGCCA | GCGAGCTAGC | CAAAGTAATT | 120 |
| GCACTTGTGG | CCGTTGACAT | CGGCAAGAGT | GATGAAATGG | CGCGAGCATT | TCCTGTGCTC | 180 |
| TGGCCGAAAA | TTTCTCCGCA | ACAGGAGTAC | TACGCCACGG | CAGTTGACTG | GTTCACCAAC | 240 |
| CCCGACGAGA | CGGTTACGTC | CTTTGATGTT | GTCGATATGC | TTGATGCAGG | CACGTCACTG | 300 |
| GATCAGGACT | TCATGACCTA | TCTGAAATGC | CTCACCGAGC | TTCATAAGCG | CCGTCGTAAA | 360 |
| TATGGATTGA | TTCTTCAGAG | GCAGCCTCTG | CCGACTATGG | TCCAAGTCTC | CCCTAGGGCG | 420 |
| CTCATGGAAT | ACGGCCCTGA | CTTTCCGCCG | GAAGCACTTG | CTTCATGGCT | CACTTGGCGC | 480 |
| AAATTCTTTT | ACGATTTGGA | CAATCGGTCT | GCACAGGAAA | CCGGCTATCT | TTTCGAACCC | 540 |
| ATCCTTGCTG | CAGCCATCGG | CGGTGAGGCG | AAGTCGGCGC | GGGAGCGTGT | GGTGAGGCGC | 600 |
| ACTGATGACC | CTACTAAGGG | TCGGCAAGTC | GACTGCTGGA | AAGTGCTGCC | GGACGGAACT | 660 |
| CCACTTGCGT | ACGAATTGAA | GTTGCGCGTG | ACGATTGCGG | CTAGCGGGCA | AGGGCGTTTT | 720 |
| GGCGAGGAGC | TCTCATTTGC | TCGCGACTGC | AGTAGTTCGG | GTGCAAAGCC | AATTCTTGTT | 780 |
| GTGCTGGATC | CCACAGAAAA | TGACAAACTG | ACCGGCTTC | AGGCCGCGTA | CCGAGAGGTG | 840 |
| GGCGGCGCCG | CTTATGTGGG | CGATGCGGCT | TGGGCTCACC | TCGAAGACGA | GGCGGGGGCA | 900 |
| ACGATGGCAT | CGTTATTGA | ACGCTATGTT | CGCGTGCCGG | TGGCTTCTGT | GTCCAGCTTT | 960 |
| GAGCGGGTTA | TCGAGGGTGA | CGCAACCAAG | CGTAGTCTCA | TCTTGCAGGA | CCTGCAGGCA | 1020 |
| CGGCTTGATG | GCAATGAACT | GACAATCTCG | CTTGGTGGCC | ATCAACGCTT | GGTCGAGCGT | 1080 |
| CATGAAGATC | AGAGTTTGGC | TGCCGATGGG | GATGATGACA | GCGAATAG | | 1128 |

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

GGCATCGTTT ATTGAACGCT ATGT                                        24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

CCCCCGCCTC GTCTTCGAGG TGAG                                        24

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

AGGAAGCTTG GAGGTTTAAA AATGACTACA CGGCAACGAC TCAGC                45

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:10:

GCCGCATGCA ACCTATTCGC TGTCATCATC CCC                33